United States Patent [19]

Tokura

[11] Patent Number: 5,293,324
[45] Date of Patent: Mar. 8, 1994

[54] METHOD AND APPARATUS FOR INSPECTING SOLDER PORTIONS USING FUZZY INFERENCE

[75] Inventor: Nobufumi Tokura, Fukuoka, Japan

[73] Assignee: Matsushita Electric Industrial Co., Ltd., Osaka, Japan

[21] Appl. No.: 867,643

[22] Filed: Apr. 13, 1992

[30] Foreign Application Priority Data

Apr. 15, 1991 [JP] Japan .................. 3-82277

[51] Int. Cl.$^5$ ............................................ G06F 15/62
[52] U.S. Cl. ............................................ 364/552
[58] Field of Search .............. 395/2, 900, 912, 916, 395/921; 364/551.01, 552, 560; 382/8, 25, 28, 34; 358/101, 106; 356/237, 376; 228/103–105; 250/559

[56] References Cited

U.S. PATENT DOCUMENTS

| | | | |
|---|---|---|---|
| 4,988,202 | 1/1991 | Nayar et al. | 356/394 |
| 5,103,105 | 4/1992 | Ikegaya et al. | 250/561 |
| 5,129,009 | 7/1992 | Lebrow | 382/8 |
| 5,130,555 | 7/1992 | Suzuki et al. | 250/559 |
| 5,134,665 | 7/1992 | Jyoko | 382/8 |
| 5,148,375 | 9/1992 | Horikami | 364/552 |
| 5,166,985 | 11/1993 | Takagi et al. | 382/8 |

OTHER PUBLICATIONS

S. Sukvittayawong and I. Inasaki, "Identification of Chip Form in Turning Process" *JSME International Journal*, vol. 34, No. 4, Dec. 1991, pp. 553–560.

*Primary Examiner*—Jack B. Harvey
*Assistant Examiner*—Thomas Peeso
*Attorney, Agent, or Firm*—Lowe, Price, LeBlanc & Becker

[57] ABSTRACT

An image of the solder portion is taken. Values of goodness/poorness judgment factors are calculated from the image of the solder portion. Grades of the goodness/poorness judgment factors are calculated from the values of the goodness/poorness judgment factors and from predetermined membership functions of the goodness/poorness judgment factors according to predetermined rules each having a condition part related to the goodness/poorness judgment factors and a conclusion part related to a goodness degree. Partial figures are calculated from predetermined membership functions of the goodness degree and from the calculated grades of the goodness/poorness judgment factors. The partial figures are combined into a final figure. A position of a centroid of the final figure is calculated. A decision is made as to whether or not the solder portion is good on the basis of the calculated position of the centroid with respect to a predetermined judgment scale.

10 Claims, 13 Drawing Sheets

METHOD AND APPARATUS FOR INSPECTING SOLDER PORTIONS USING FUZZY INFERENCE

BACKGROUND OF THE INVENTION

1. Field of the Invention

This invention relates to a method of automatically inspecting a solder portion of a printed circuit board or others. This invention also relates to an apparatus for automatically inspecting a solder portion of a printed circuit board or others.

2. Description of the Prior Art

It is known to automatically inspect solder portions of a printed circuit board. In a prior art apparatus, each of solder portions is observed by a camera, and a signal representing an image of the solder portion is generated by the camera. A computer processes the image signal, calculating the values of goodness/poorness judgment factors such as the length, the width, and the area of a dark region or a bright region on the basis of the distribution of the luminance of the image. The calculated values are compared with reference values to decide whether the solder portion is good or poor.

In the prior art apparatus, each of the calculated values of the goodness/poorness judgment factors is subjected to judgment through the comparison with the related reference value. In the case where all the goodness/poorness judgment factors are judged to be acceptable, the solder portion is finally decided to be good. In the case where at least one of the goodness/poorness judgment factors is judged to be unacceptable while the other goodness/poorness judgment factors are judged to be acceptable, the solder portion is finally decided to be poor. Since some of good solder portions have an unacceptable judgment factor although the other judgment factors are acceptable, the final decision regarding the solder portion tends to be low in accuracy.

Some of solder portions are in a gray zone between a good zone and a poor zone. It is generally difficult to execute accurate and reliable decision regarding such gray-zone solder portions. It is better to execute closer inspection of gray-zone solder portions.

SUMMARY OF THE INVENTION

It is an object of this invention to provide an improved method of automatically inspecting a solder portion.

It is another object of this invention to provide an improved apparatus for automatically inspecting a solder portion.

A first aspect of this invention provides a method of inspecting a solder portion which comprises taking an image of the solder portion; calculating values of goodness/poorness judgment factors from the image of the solder portion; calculating grades of the goodness/poorness judgment factors from the calculated values of the goodness/poorness judgment factors and from predetermined membership functions of the goodness/poorness judgment factors according to predetermined rules each having a condition part related to the goodness/poorness judgment factors and a conclusion part related to a goodness degree; calculating partial figures from predetermined membership functions of the goodness degree and from the calculated grades of the goodness/poorness judgment factors; combining the partial figures into a final figure; calculating a position of a centroid of the final figure; and deciding whether or not the solder portion is good on the basis of the calculated position of the centroid with respect to a predetermined judgment scale.

A second aspect of this invention provides an apparatus for inspecting a solder portion which comprises means for taking an image of the solder portion; means for calculating values of goodness/poorness judgment factors from the image of the solder portion; means for calculating grades of the goodness/poorness judgment factors from the calculated values of the goodness/poorness judgment factors and from predetermined membership functions of the goodness/poorness judgment factors according to predetermined rules each having a condition part related to the goodness/poorness judgment factors and a conclusion part related to a goodness degree; means for calculating partial figures from predetermined membership functions of the goodness degree and from the calculated grades of the goodness/poorness judgment factors; means for combining the partial figures into a final figure; means for calculating a position of a centroid of the final figure; and means for deciding whether or not the solder portion is good on the basis of the calculated position of the centroid with respect to a predetermined judgment scale.

A third aspect of this invention provides an apparatus for inspecting a solder portion which comprises means for detecting a condition of the solder portion; means for calculating a first grade from the condition of the solder portion which is detected by the detecting means in accordance with a first predetermined membership function which determines a relation between the first grade and the condition of the solder portion; means for calculating a first parameter representative of a goodness degree from the first grade calculated by the first-grade calculating means and from a second predetermined membership function corresponding to a first rule which has a condition part related to the condition of the solder portion and a conclusion part related to the goodness degree; means for calculating a second grade from the condition of the solder portion which is detected by the detecting means in accordance with a third predetermined membership function which determines a relation between the second grade and the condition of the solder portion; means for calculating a second parameter representative of the goodness degree from the second grade calculated by the second-grade calculating means and from a fourth predetermined membership function corresponding to a second rule which has a condition part related to the condition of the solder portion and a conclusion part related to the goodness degree; and means for deciding whether the solder portion is good or poor in response to the first parameter calculated by the first-parameter calculating means and the second parameter calculated by the second-parameter calculating means.

A fourth aspect of this invention provides an apparatus for inspecting a solder portion which comprises means for detecting a first condition of the solder portion; means for deciding whether the solder portion is good, poor, or gray in response to the detected first condition of the solder portion; means for, when the solder portion is decided to be gray, detecting a second condition of the solder portion; and means for deciding whether the solder portion is good or poor in response to the detected second condition of the solder portion.

DESCRIPTION OF THE PREFERRED EMBODIMENT

Figure 1:
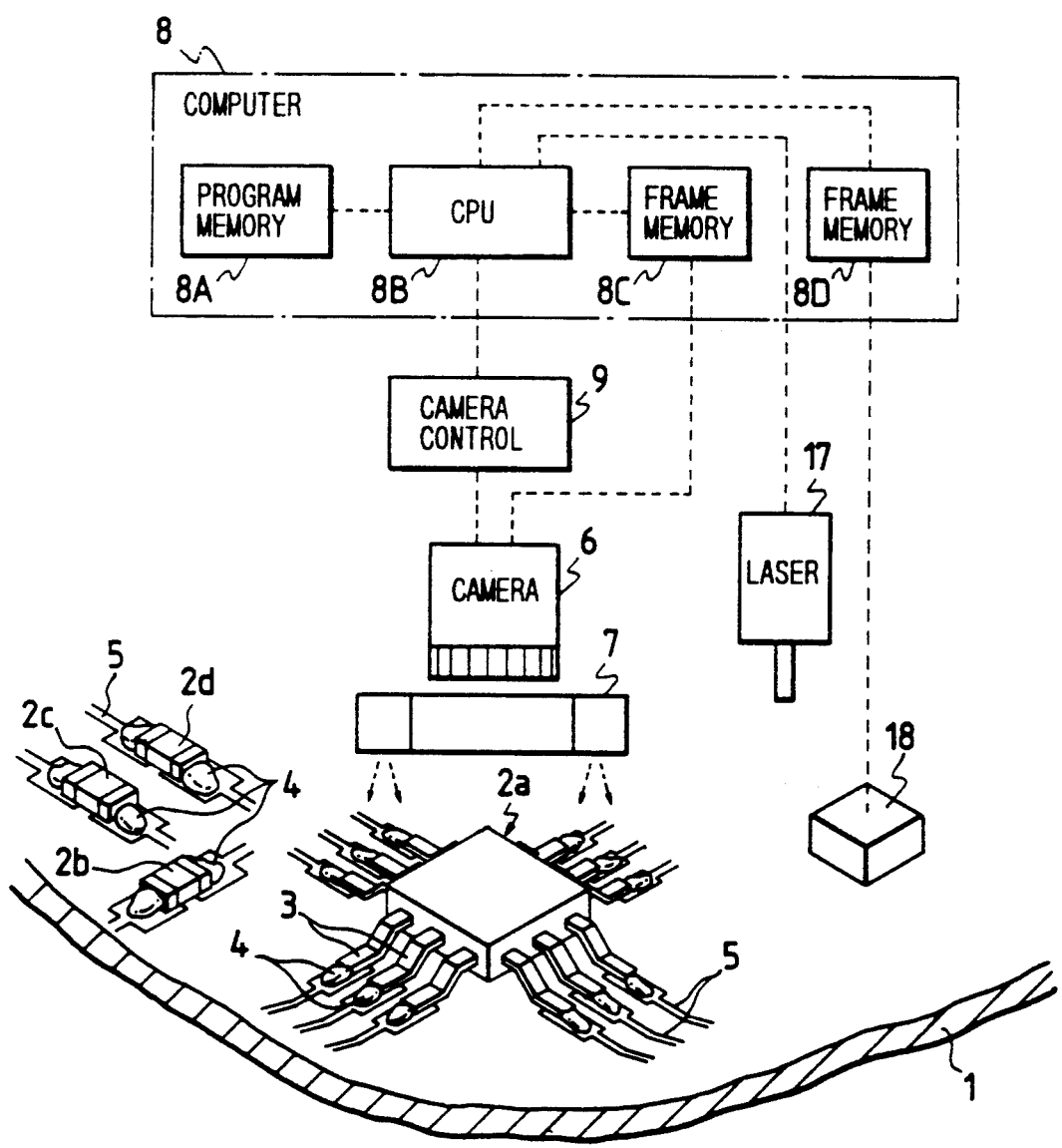
FIG. 1 is a diagram of an apparatus for automatically inspecting a solder portion according to an embodiment of this invention.

With reference to FIG. 1, a circuit board 1 is provided with electronic parts (QFPs, capacitor chips, resistor chips, and others) 2a, 2b, 2c, and 2d each having leads 3 which are soldered at portions 4 to given points of a circuit pattern 5 respectively. The electronic parts are also denoted by the reference numeral 2.

A CCD camera 6 and a light source 7 are located above the circuit board 1. The electronic parts 2 are illuminated by the light source 7. Portions of the light emitted from the light source 7 are reflected at the electronic parts 2 including the solder portions 4, and portions of the reflected light are incident to the camera 6. A solder portion 4 is observed by the camera 6, and data representing an image of the solder portion 4 is generated by the camera 6. The image data is fed from the camera 6 to a computer 8. A two-dimensional horizontal drive mechanism (not shown) move the camera 6 and the circuit board 1 relative to each other in response to an instruction from the computer 8, so that solder portions 4 can be sequentially observed by the camera 6. The camera 6, the light source 7, and the computer 8 compose a first or primary inspection device using fuzzy inference.

The computer 8 includes a combination of a program memory 8A, a CPU 8B, and frame memories 8C and 8D. The CPU 8B includes a processing section and a RAM. The CPU 8B is connected to the camera 6 via a camera control unit 9 to control the camera 6. The image data fed from the camera 6 is written into the frame memory 8C.

Figure 4:
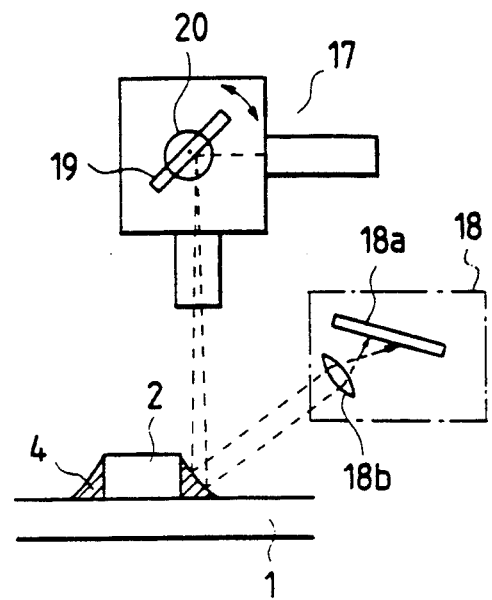
FIG. 4 is a diagram of the laser illumination device, the light receiver, and the circuit board in the apparatus of FIG. 1.

As shown in FIGS. 1 and 4, a laser illumination device 17 and a light receiver 18 are located above the circuit board 1. The light receiver 18 includes an optical position sensor 18a and an optical condenser 18b. A beam of light emitted from the laser illumination device 17 is applied to a mirror 19, being reflected by the mirror 19 toward a solder portion 4 on the circuit board 1 and being applied to the solder portion 4. The laser light beam is reflected or scattered by the solder portion 4, being incident to the optical condenser 18b and being condensed on the optical position sensor 18a by the optical condenser 18b.

The position of a spot of the laser light beam on the optical position sensor 18a depends on the height of the point of the surface of the solder portion 4 at which the laser light beam is scattered. This height is measured from the basic flat plane of the circuit board 1. The optical position sensor 18a detects the position of the spot of the laser light beam and outputs an electric signal representative of the position of the spot of the laser light beam, that is, the height of the point of the surface of the circuit board 1 at which the laser light beam is scattered. The light receiver 18 further includes an A/D converter which converts the electric position signal into corresponding position (height) data. The position (height) data is fed from the light receiver 18 to the computer 8, being written into the frame memory 8D.

The angle of the mirror 19 with respect to the laser illumination device 17 is varied by a motor 20 so that the upper surface of the laser portion 4 can be linearly scanned by the laser light beam.

The laser illumination device 17, the light receiver 18, and the computer 8 compose a second or close inspection device which is of a non-fuzzy type. It should be noted that the close inspection device may be formed by an X-ray measurement device, an infrared-ray measurement device, or a contact-type three-dimensional measurement device.

Figure 2:
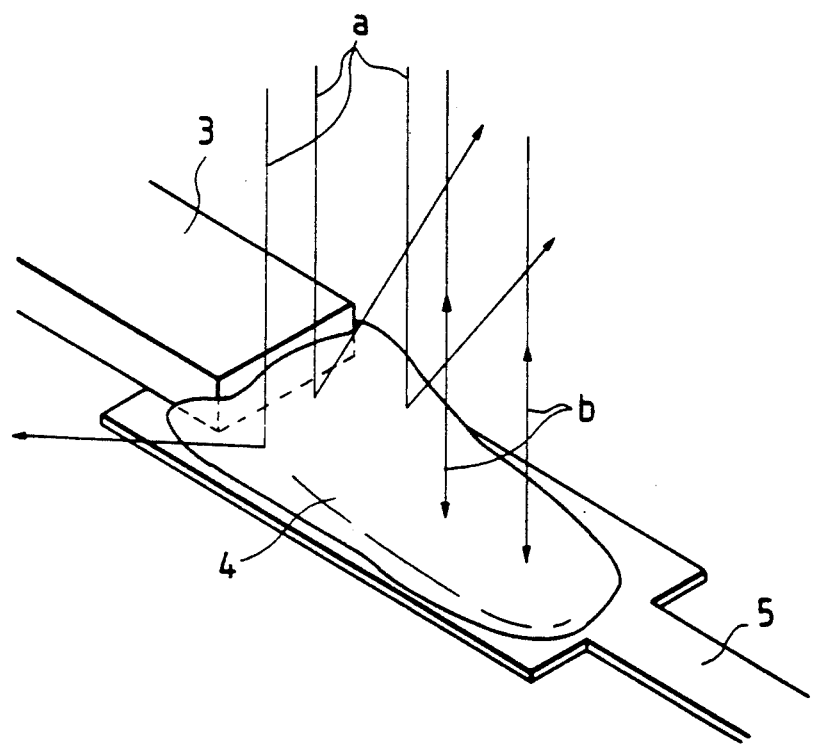
FIG. 2 is a perspective view of a solder portion, leads, and a portion of a circuit pattern on a circuit board.
Figure 3:
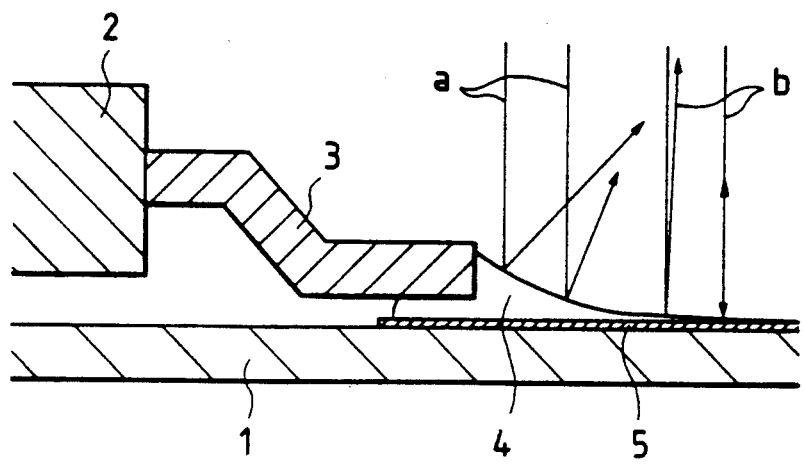
FIG. 3 is a sectional view of the solder portion, the leads, the portion of the circuit pattern, and the circuit board in FIG. 2.
Figure 5:
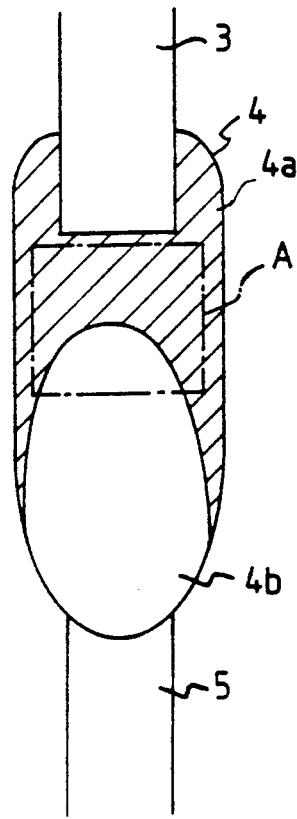
FIG. 5 is a plan view of a solder portion, leads, and a portion of a circuit pattern on a circuit board.

As shown in FIGS. 2 and 3, beams "a" and "b" of the light emitted from the light source 7 (see FIG. 1) are applied to a solder portion 4. In general, solder portions 4 have mirror-like surfaces with varying slopes. In FIGS. 2 and 3, the light beam "a" applied to a steep-slope surface of the solder portion 4 is reflected sideward and goes away from the camera 6, so that the steep-slope surface of the solder portion 4 looks like a dark region through the camera 6. The light beam "b" applied to a gentle-slope surface of the solder portion 4 is reflected upward and is incident to the camera 6, so that the gentle-slope surface of the solder portion 4 looks like a bright region through the camera 6. In FIG. 5, a checked region 4a agrees with such a dark region while a non-checked region 4b agrees with such a bright region. As shown in FIG. 5, a window area "A" inspected via the camera 6 is set so as to extend on and around the boundary between the dark region 4a and the bright region 4b.

Figure 6:
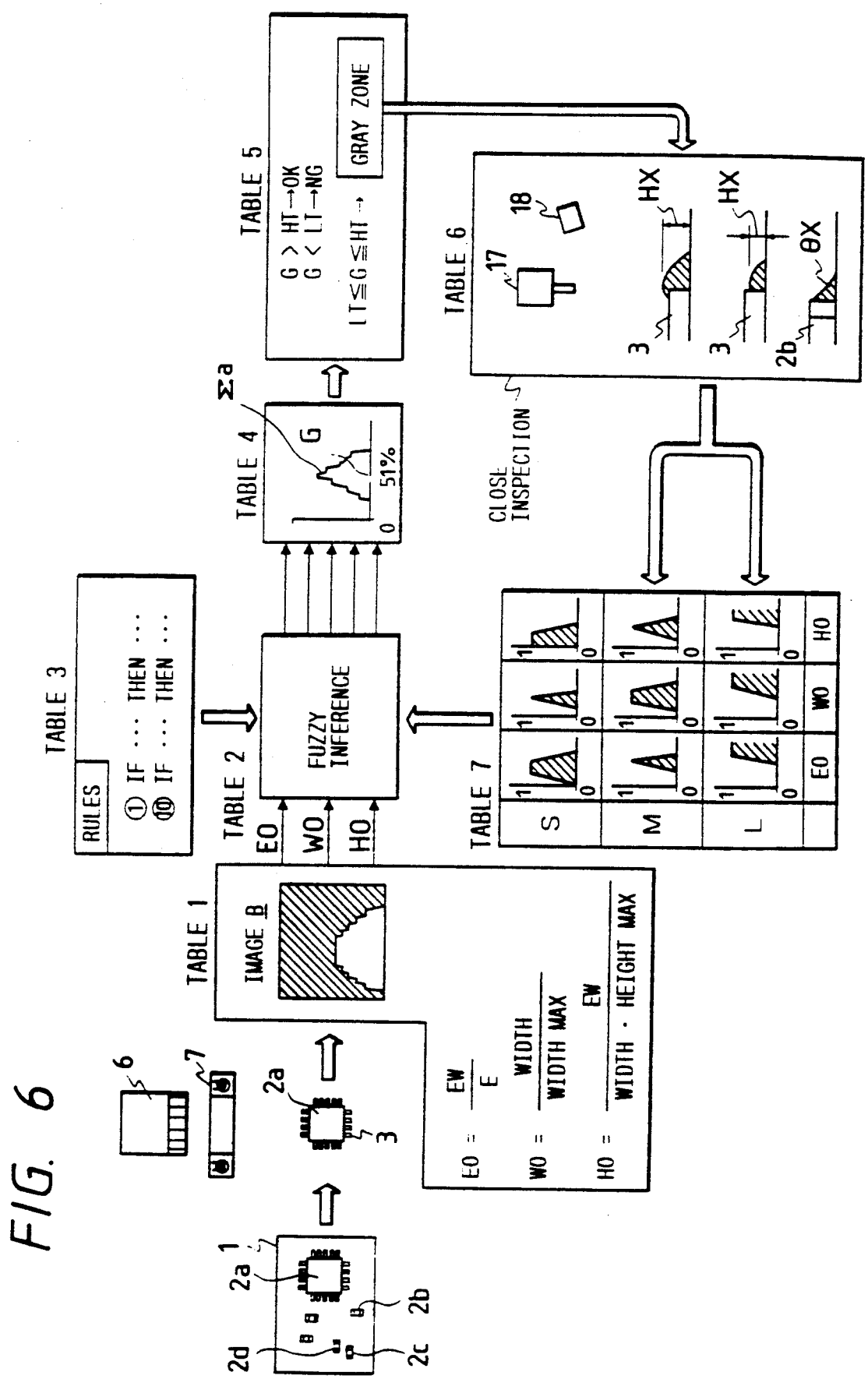
FIG. 6 is a function flow diagram of the apparatus of FIG. 1.

The computer 8 operates in accordance with a program stored in the memory 8A. The operation of the computer 8 will be described hereinafter. With reference to FIG. 6, the computer 8 controls the camera 6 so that the inspection area "A" will be set at the end of the leads 3 of the electronic parts 2a on the circuit board 1 and that the camera 6 will take an image "B" of a solder portion 4 which extends in the inspection area "A". This process by the computer 8 is illustrated in TABLE 1 of FIG. 6. The camera 6 outputs data representative of the image "B" to the computer 8. The data of the image "B" is written into the frame memory 8C.

The computer 8 calculates the values of goodness/poorness judgment factors EO, WO, and HO from the data of the image "B", and decides whether the solder portion 4 is good, poor, or gray on the basis of the calculated values of the judgment factors EO, WO, and HO through fuzzy reasoning or fuzzy inference. This process by the computer 8 is illustrated in TABLE 2 of FIG. 6. The goodness/poorness decision is made on the basis of the position of the centroid "G" of a final composite shape (figure) Σa which is illustrated in TABLE 4 of FIG. 6. The calculation of the final composite shape Σa will be explained later.

In TABLE 5 of FIG. 6, the computer 8 compares the position of the centroid "G" with a high predetermined threshold HT and a low predetermined threshold LT. When G>HT, the computer 8 decides the solder portion 4 to be good. When G<LT, the computer 8 decides the solder portion 4 to be poor. When LT≦G≦HT, the computer 8 decides the solder portion 4 to be in a gray zone and then activates the close inspection device including the laser illumination device 17 and the light receiver 18.

Figure 7:
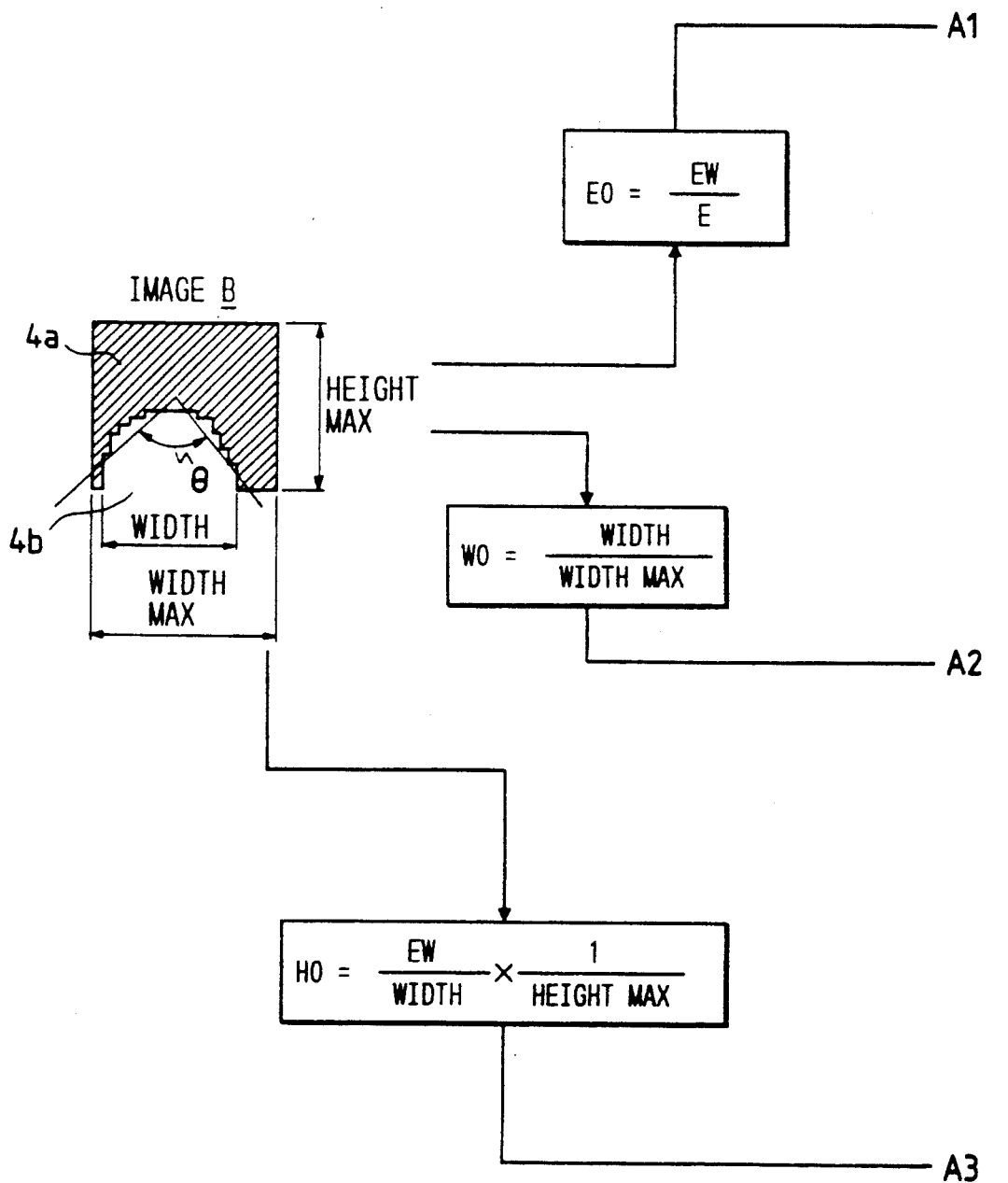
FIGS. 7-9 are function flow diagrams showing fuzzy inference executed in the apparatus of FIG. 1.
Figure 8:
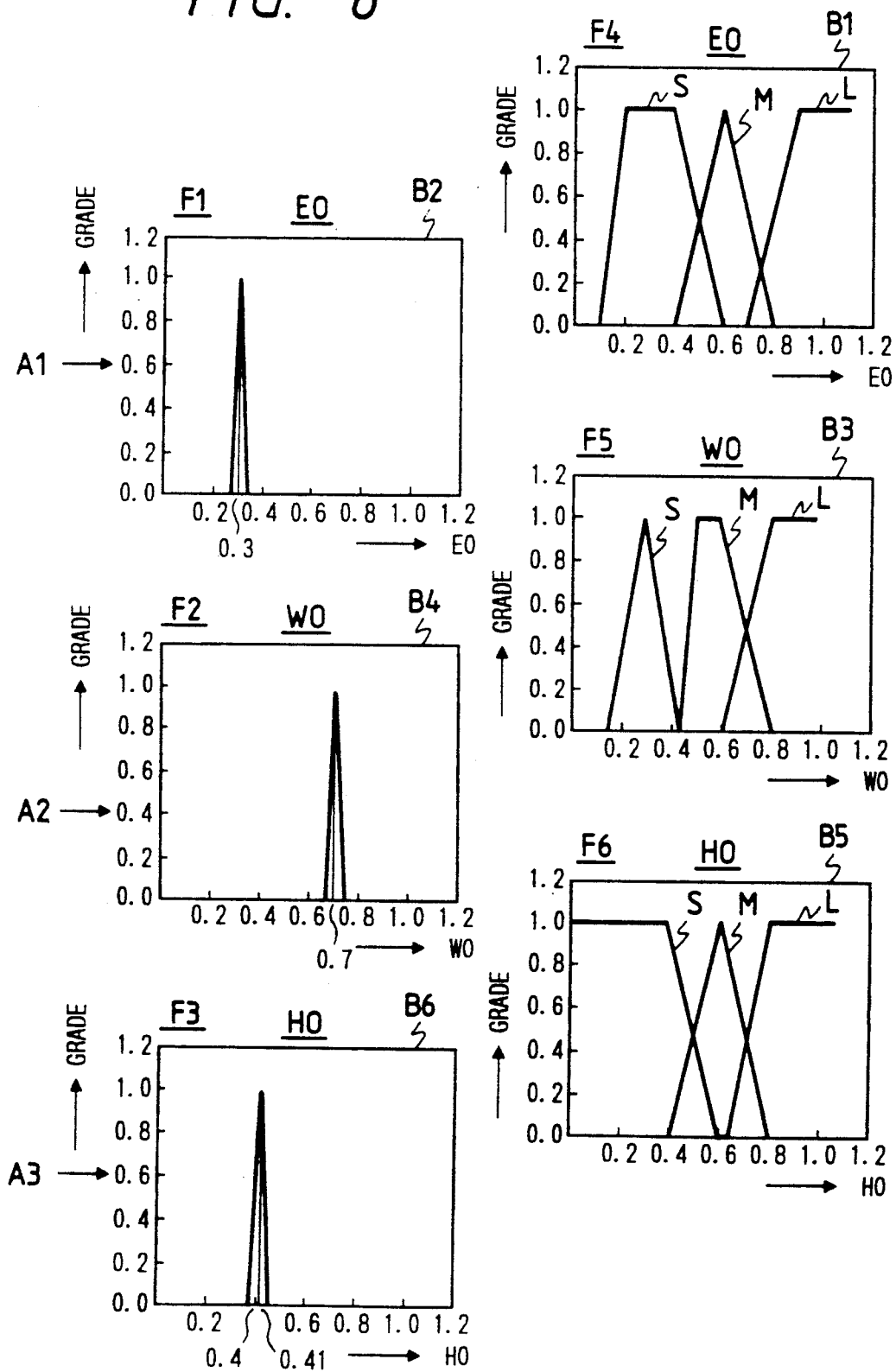
Figure 9:
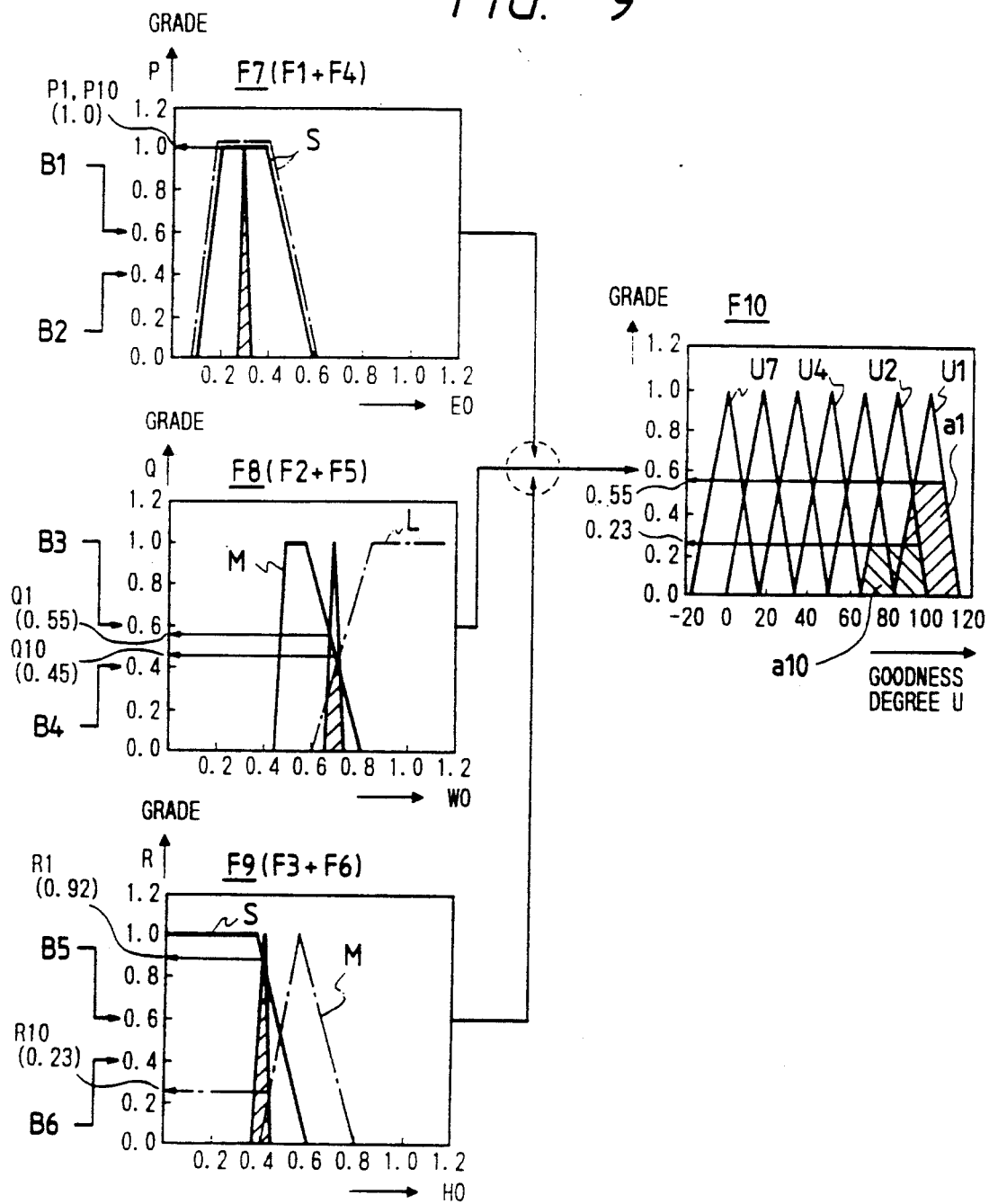

FIGS. 7-9 show the process of deciding whether the solder portion 4 is good, poor, or gray through fuzzy inference. The contents of FIGS. 7-9 are continuously connected along lines A1-A3 and B1-B6. In FIG. 7, the image "B" represented by the data is a bi-level image of the inspection area "A" of FIG. 5. The computer 8 calculates the length of the image "B" (which is denoted by "height max"), the width of the image "B" (which is denoted by "width max"), and the width of the bright region 4b (which is denoted by "width") which are basic factors. The total area of the image "B", that is, "height max"×"width max", is denoted by "E". The area of the bright region 4b in the inspection zone "A" is denoted by EW.

The computer 8 calculates the values of goodness/poorness judgment factors, that is, an area factor EO, a width factor WO, and a length factor HO, on the basis of the basic factors and the conditions of the image "B" by referring to the following equations.

$$EO = EW/E \quad (1)$$

$$WO = \text{width}/\text{width max} \quad (2)$$

$$HO = (EW/\text{width})\cdot(1/\text{height max}) \quad (3)$$

Regarding the equation (3), the term "EW/width" corresponds to the average length of the bright region 4b and the term "height max" corresponds to the length of the image "B", so that the factor HO agrees with the ratio between the length of the image "B" and the average length of the bright region 4b.

It should be noted that the vertical angle θ of the bright region 4b may be used as a basic factor.

Data representing predetermined goodness/poorness judgment rules 1-10 is previously registered in the program memory 8A of the computer 8. Each of the rules 1-10 has a condition part and a conclusion part, and is expressed as "if xx is AA, then yy is BB". The rules are roughly shown in TABLE 3 of FIG. 6. The details of the rules 1-10 will be given in the following.

Rule 1: If EO is small (S) and WO is middle (M), and HO is small (S), then an inspected solder portion may be good at a very high possibility (U1).

Rule 2: If EO is small (S) and WO is large (L), and HO is small (S), then an inspected solder portion may be good at a very high possibility (U1).

Rule 3: If EO is middle (M) and WO is small (S), and HO is large (L), then an inspected solder portion may be good at an intermediate possibility (U4).

Rule 4: If EO is large (L) and WO is middle (M), and HO is small (S), then an inspected solder portion may be good at a somewhat low possibility (U5).

Rule 5: If EO is large (L) and WO is large (L), and HO is large (L), then an inspected solder portion may be good at a very low possibility (U7).

Rule 6: If EO is large (L) and WO is small (S), and HO is middle (M), then an inspected solder portion may be good at a somewhat high possibility (U3).

Rule 7: If EO is small (S) and WO is small (S), and HO is large (L), then an inspected solder portion may be good at a very low possibility (U7).

Rule 8: If EO is middle (M) and WO is middle (M), and HO is small (S), then an inspected solder portion may be good at a considerably low possibility (U6).

Rule 9: If EO is small (S) and WO is small (S), and HO is large (L), then an inspected solder portion may be good at a very low possibility (U7).

Rule 10: If EO is small (S) and WO is large (L), and HO is middle (M), then an inspected solder portion may be good at a considerably high possibility (U2).

The portions F1, F2, and F3 of FIG. 8 show functions determining the relations of the values of the goodness/poorness judgment factors EO, WO, and HO with a grade (degree). Under conditions shown in FIG. 8, the values of the judgment factors EO, WO, and HO, which are calculated by referring to the equations (1), (2), and (3), are equal to 0.3, 0.7, and 0.41 respectively. In the portions F1, F2, and F3 of FIG. 8, the relation-representing lines of the functions form triangular shapes which spread around the values of 0.3, 0.7, and 0.41 and thus which have certain widths in view of errors caused by noise. It should be noted that the triangular-shape functions are denoted by F1, F2, and F3 also.

The portions F4, F5, and F6 of FIG. 8 show predetermined membership functions related to the goodness/poorness judgment factors EO, WO, and HO. As shown in the portion F4 of FIG. 8, there are three different membership functions for the goodness/poorness judgment factor EO which correspond to "small (S)", "middle (M)", and "large (L)" respectively. As shown in the portion F5 of FIG. 8, there are three different membership functions for the goodness/poorness judgment factor WO which correspond to "small (S)", "middle (M)", and "large (L)" respectively. As shown in the portion F6 of FIG. 8, there are three different membership functions for the goodness/poorness judgment factor HO which correspond to "small (S)", "middle (M)", and "large (L)" respectively. Data representing these membership functions are previously registered in the program memory 8A of the computer 8.

The portions F7, F8, and F9 of FIG. 9 show the superimposition of the portions F1 and F4 of FIG. 8, the superimposition of the portions F2 and F5 of FIG. 8, and the superimposition of the portions F3 and F6 of FIG. 8 respectively.

FIGS. 8 and 9 show an exemplary case in which the condition part of the rule 1 is best satisfied, that is, the values of the goodness/poorness factors EO, WO, and HO are small (S), middle (M), and small (S) respectively. Hereinafter, a description will be given of the calculation using the rule 1.

As shown in the portion F7 of FIG. 9, regarding the goodness/poorness judgment factor EO, the computer 8 calculates the grade P1 at a point of intersection between the relation-representing triangle (the triangular-shape function F1 of FIG. 8) and the membership function "S" (the portion F4 of FIG. 8). The calculated grade P1 is equal to 1.0. As shown in the portion F8 of FIG. 9, regarding the goodness/poorness judgment factor WO, the computer 8 calculates the grade Q1 at a point of intersection between the relation-representing triangle (the triangular-shape function F2 of FIG. 8) and the membership function "M" (the portion F5 of FIG. 8). The calculated grade Q1 is equal to 0.55. As shown in the portion F9 of FIG. 9, regarding the goodness/poorness judgment factor HO, the computer 8 calculates the grade R1 at a point of intersection between the relation-representing triangle (the triangular-shape function F3 of FIG. 8) and the membership function "S" (the portion F6 of FIG. 8). The calculated grade R1 is equal to 0.92.

The portion F10 of FIG. 9 shows seven different predetermined membership functions U1–U7 related to the degree "U" of the goodness of an inspected solder portion. The membership function U1 corresponds to the fact that an inspected solder portion may be good at a very high possibility. The membership function U2 corresponds to the fact that an inspected solder portion may be good at a considerably high possibility. The membership function U3 corresponds to the fact that an inspected solder portion may be good at a somewhat high possibility. The membership function U4 corresponds to the fact that an inspected solder portion may be good at an intermediate possibility. The membership function U4 corresponds to the fact that an inspected solder portion may be good at a somewhat low possibility. The membership function U6 corresponds to the fact that an inspected solder portion may be good at a considerably low possibility. The membership function U7 corresponds to the fact that an inspected solder portion may be good at a very low possibility. The data representing the membership functions U1–U7 are previously registered in the program memory 8A of the computer 8.

As understood from the previous description of the details of the rules 1–10, the condition part of each rule is determined by the magnitudes of the goodness/poorness judgment factors EO, WO, and HO, and the conclusion part thereof agrees with the goodness degree "U" (U1–U7).

In view of a safety factor, the smallest member of the calculated grades P1, Q1, and R1 is selected. Specifically, the grade Q1 (0.55) is selected. According to the rule 1, the goodness-degree membership function U1 is selected. As shown in FIG. 9, a determination is given of a partial region (figure) a1 which is defined between the lines of the membership function U1 and which extends below the horizontal line corresponding to a grade of 0.55.

Next, calculations similar to the above-mentioned calculations are executed according to, for example, the rule 10 which corresponds the fact that the goodness/poorness judgment factors EO, WO, and HO are small (S), large (L), and middle (M) respectively.

As shown in the portion F7 of FIG. 9, regarding the goodness/poorness judgment factor EO, the computer 8 calculates the grade P10 at a point of intersection between the relation-representing triangle (the triangular-shape function F1 of FIG. 8) and the membership function "S" (the portion F4 of FIG. 8). The calculated grade P10 is equal to 1.0. As shown in the portion F8 of FIG. 9, regarding the goodness/poorness judgment factor WO, the computer 8 calculates the grade Q10 at a point of intersection between the relation-representing triangle (the triangular-shape function F2 of FIG. 8) and the membership function "L" (the portion F5 of FIG. 8). The calculated grade Q10 is equal to 0.45. As shown in the portion F9 of FIG. 9, regarding the goodness/poorness judgment factor HO, the computer 8 calculates the grade R10 at a point of intersection between the relation-representing triangle (the triangular-shape function F3 of FIG. 8) and the membership function "M" (the portion F6 of FIG. 8). The calculated grade R10 is equal to 0.23.

In view of a safety factor, the smallest member of the calculated grades P10, Q10, and R10 is selected. Specifically, the grade R10 (0.23) is selected. According to the rule 10, the goodness-degree membership function U2 is selected. As shown in FIG. 9, a determination is given of a partial region (figure) a10 which is defined between the lines of the membership function U2 and which extends below the horizontal line corresponding to a grade of 0.23.

Figure 10:
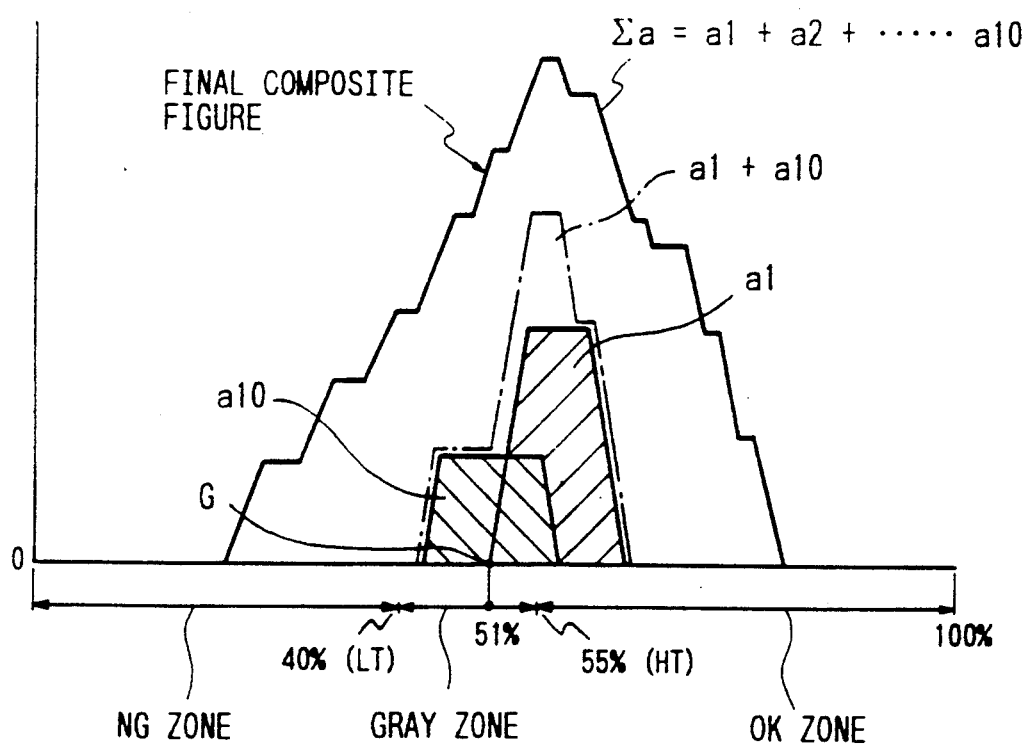
FIG. 10 is a diagram showing partial figures and a final composite figure.

As shown in FIG. 10, the determined partial regions a1 and a10 are added and combined. Similarly, partial regions a2, a3, a4, a5, a6, a7, a8, and a9 are determined in connection with the rules 2, 3, 4, 5, 6, 7, 8, and 9 respectively. The partial regions a1, 2, a3, a4, a5, a6, a7, a8, a9, and a10 are added and combined into a final composite shape or figure Σa (see TABLE 4 of FIG. 6). The partial regions a1, 2, a3, a4, a5, a6, a7, a8, a9, and a10 are parameters representing the goodness degree.

With reference to FIG. 10 and also TABLE 4 of FIG. 6, the computer 8 calculates the final accumulative shape Σa and the position of the centroid G of the final composite shape Σa. The computer 8 decides whether an inspected solder potion is good, poor, or gray on the basis of the calculated position of the centroid G. As shown in FIG. 10, a predetermined judgment scale has a range of 0% to 100% in which the centroid G can exist, and the range is divided into an OK zone, a gray zone, and a NG zone by a high predetermined threshold HT of 55% and a low predetermined threshold LT of 40%. Specifically, the OK zone corresponds to values greater than 55%. The gray zone corresponds to a range of 40% to 55%. The NG zone corresponds to values smaller than 40%. The OK zone represents that an inspected solder portion is decided to be good. The NG zone represents that an inspected solder portion is decided to be poor. Data representing the high threshold HT and the low threshold LT is previously registered in the program memory 8A of the computer 8.

As shown in TABLE 5 of FIG. 6, an inspected solder portion is decided to be good (OK) when $G > HT$. The inspected solder portion is decided to be poor (NG) when $G < LT$. At this stage, the poorness/goodness decision of the inspected solder region is not completed in the case where $LT \leq G \leq HT$.

In the case where $LT \leq G \leq HT$, that is, in the case where the centroid G is in the gray zone, the computer 8 activates the close inspection device including the laser illumination device 17 and the light receiver 18 (see TABLE 6 of FIG. 6). Under the conditions shown in FIG. 10, the value of the position of the centroid G is equal to 51% in the gray zone.

Figure 11:
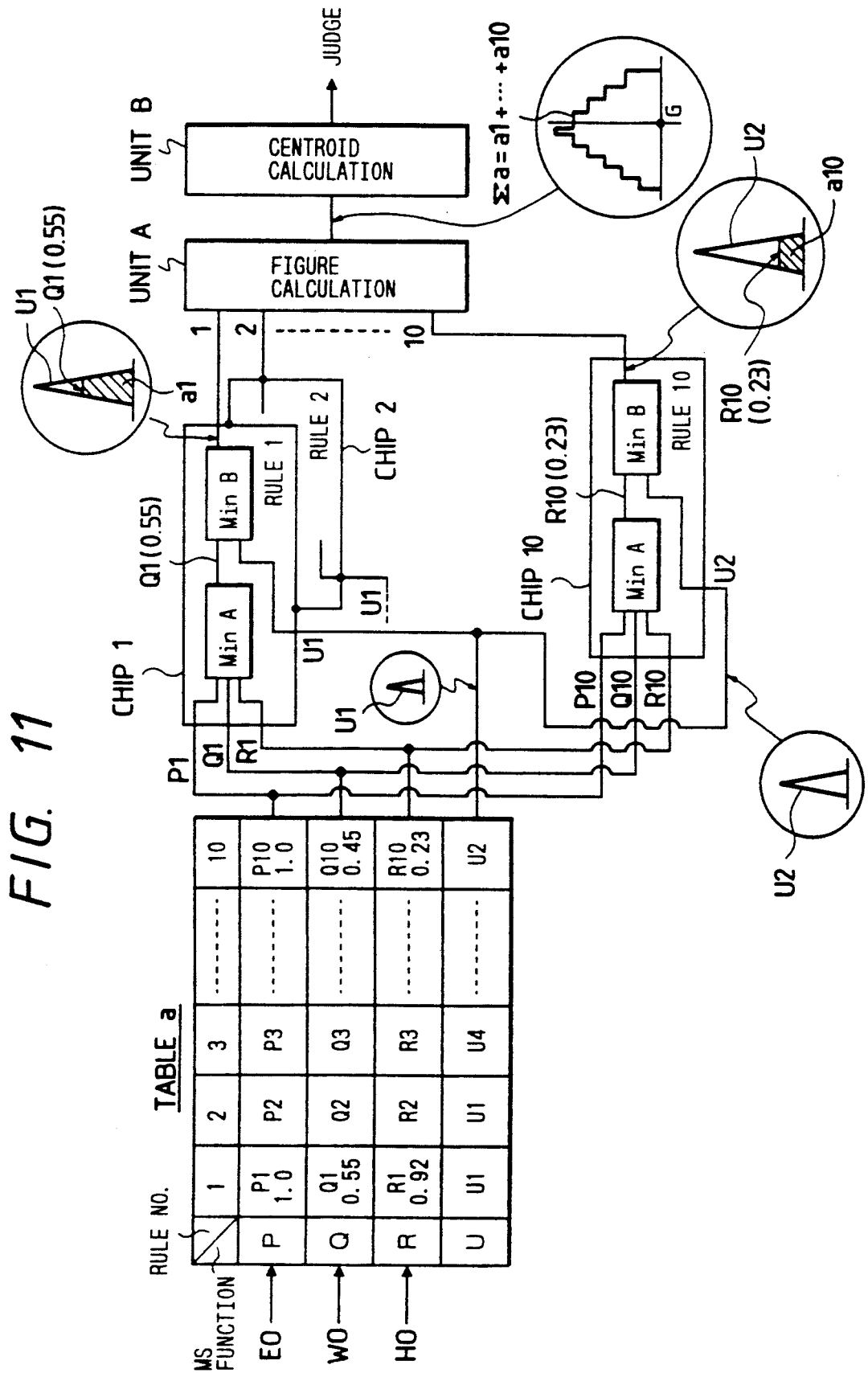
FIG. 11 is a function flow diagram of the apparatus of FIG. 1.

With reference to FIG. 11, the portion TABLEa denotes the goodness degree "U" and the goodness/poorness judgment factors EO, WO, and HO expressed in the rules 1–10. The portions CHIP1–CHIP10 execute calculations using the rules 1–10 respectively. It should be noted that the portions CHIP2–CHIP9 are omitted from FIG. 11. Each portion MinA selects the minimum member of the grades P, Q, and R inputted from the portion TABLEa. The portions MinB calculates the partial regions a1, a2, . . . , a10 from the minimum grades selected by the portions MinA and the conclusions "U". The portion UnitA adds and combines the calculated partial regions a1, a2, . . . , a10 into the final composite shape Σa. The portion UnitB calculates the position of the centroid G of the final composite shape Σa.

As described previously, in the case where LT≦G≦HT, that is, in the case where the centroid G is in the gray zone, the computer 8 activates the close inspection device including the laser illumination device 17 and the light receiver 18 (see TABLE 6 of FIG. 6). During the scanning process, the cross-section of a solder portion 4 is measured by the close inspection device. It should be noted that the close inspection device also includes the computer 8.

Figure 12:
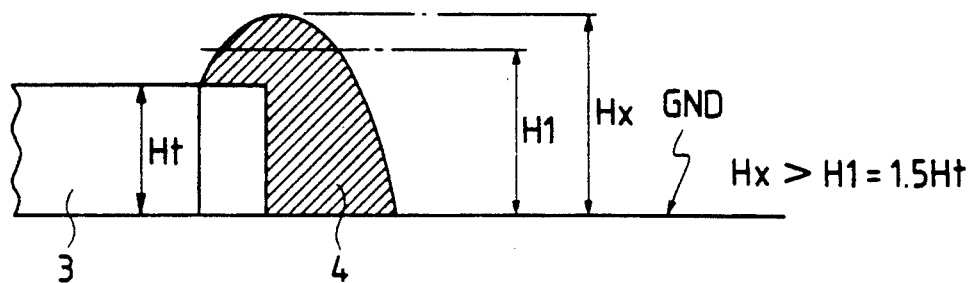
FIGS. 12-14 are diagrams showing the cross-sections of poor solder portions respectively.
Figure 13:
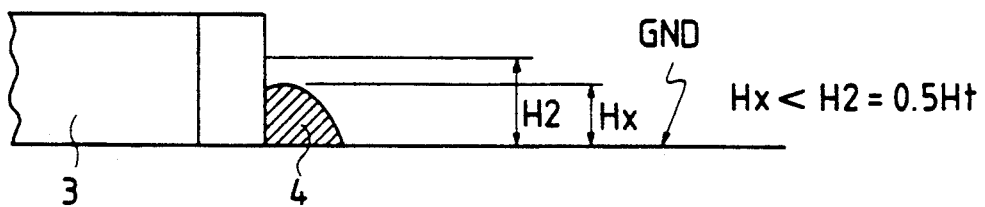
Figure 14:
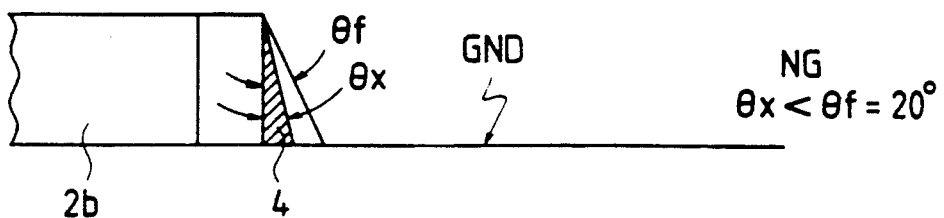

FIGS. 12-14 show examples of the cross-sections of poor solder portions 4 which are measured by the close inspection device. With reference to FIGS. 12-14, the upper flat surface of the circuit board 1 is defined as a reference plane GND, and measurement is given of the height Hx of a solder portion 4 relative to the reference plane GND. The light receiver 18 outputs data representing the measured value of the height Hx which is stored into the frame memory 8D. The computer 8 compares the measured height Hx with predetermined upper and lower limit heights H1 and H2 to decide whether the inspected solder portion 4 is good or poor. Data representing the upper and lower limit heights H1 and H2 is previously registered in the program memory 8A of the computer 8. For example, the upper limit height H1 is equal to the thickness Ht of the leads 3 which is multiplied by 1.5. The lower limit height H2 is equal to the thickness Ht of the leads 3 which is multiplied by 0.5. When the measured height Hx is greater than the upper limit height H1 as shown in FIG. 12, the amount of solder is judged to be excessively large and the inspected solder portion 4 is decided to be poor. When the measured height Hx is smaller than the lower limit height H2 as shown in FIG. 13, the amount of solder is judged to be too small and the inspected solder portion 4 is decided to be poor. When the measured height Hx exists between the upper limit height and the lower limit height H2, the inspected solder portion 4 is decided to be good.

The computer 8 processes the height data outputted from the light receiver 18, measuring the angle θx of the inclination of the inspected solder portion 4 as shown in FIG. 14. The computer 8 compares the measured inclination angle θx with a predetermined reference angle θf to decide whether the inspected solder portion 4 is good or poor. Data representing the reference angle θf is previously registered in the program memory 8A of the computer 8. For example, the reference angle θf is equal to 20 degrees. When the measured inclination angle θx is smaller than the reference angle θf as shown in FIG. 14, the inspected solder portion 4 is decided to be poor. Otherwise, the inspected solder portion 4 is decided to be good.

It should be noted that the upper surface of an inspected solder portion may be two-dimensionally scanned by the laser light beam to measure the three-dimensional shape of the inspected solder portion, and that the measured three-dimensional shape of the inspected solder portion may be used in the decision of whether the inspected solder portion is good or poor.

As described previously, a solder portion in the gray zone, which is not decided in goodness/poorness by fuzzy inference, is subjected to the close inspection using the laser illumination device 17 (see TABLE 6 of FIG. 6). In the case where the inspected solder portion is decided to be good during the close inspection, the computer 8 corrects the membership functions so that the value of the position of the centroid G will be greater than the high threshold HT (55% in FIG. 10). In the case where the inspected solder portion is decided to be poor during the close inspection, the computer 8 corrects the membership functions so that the value of the position of the centroid G will be smaller than the low threshold LT (40% in FIG. 10). The membership-function correcting process corresponds to TABLE 7 of FIG. 6. For example, the correction of the membership functions is executed by changing the shapes and the positions of the figures defined by the membership functions shown in FIGS. 8 and 9. The rules 1-10 may be changed in place of the correction of the membership functions.

After the membership functions are corrected as described previously, a later inspected solder portion similar to the previous gray-zone solder portion can be immediately decided to be good or poor by the primary inspection using the camera 6 without executing the close inspection using the laser illumination device 17.

Figure 15:
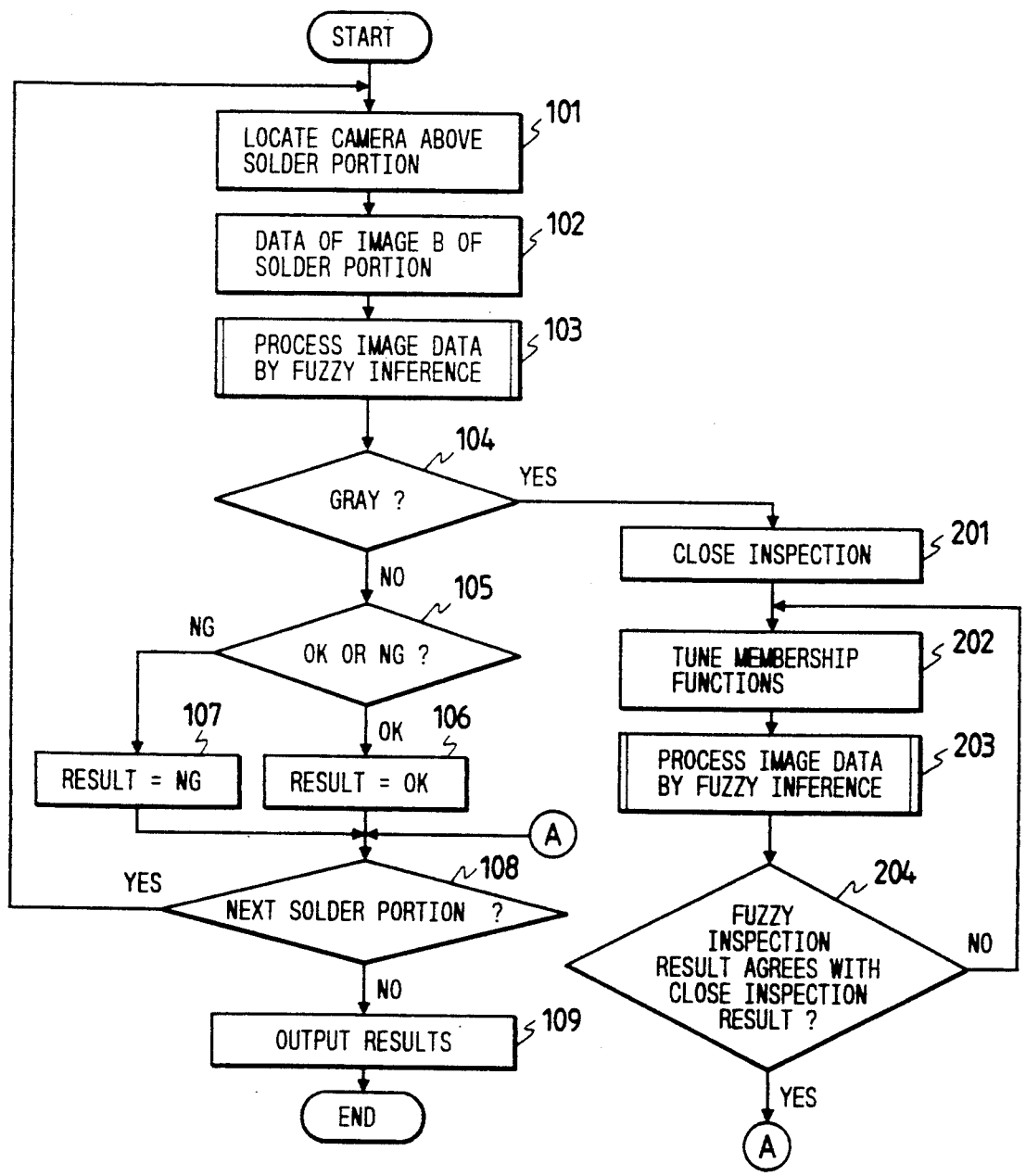
FIG. 15 is a flowchart of the program controlling the computer of FIG. 1.

As described previously, the computer 8 operates in accordance with the program stored in the memory 8A. FIG. 15 is a flowchart of the program.

As shown in FIG. 15, a first step 101 of the program activates the two-dimensional horizontal drive mechanism (not shown) so that the camera 6 will be moved, relative to the circuit board 1, to a position directly above a solder portion 4 to be inspected. A step 102 following the step 101 activates the camera 6 so that the camera 6 will take an image "B" of the solder portion 4. The camera 6 outputs the data representative of the image "B" which is stored into the frame memory 8C.

A block 103 following the step 102 processes the data of the image "B" in accordance with fuzzy inference, and thereby calculates a final composite shape (figure) Σa and the position of the centroid G of the final composite shape Σa. The details of the block 103 will be explained later. A step 104 following the block 103 decides whether or not the calculated position of the centroid G is in the gray zone. When the position of the centroid G is decided to be in the gray zone, the program advances to a step 201. Otherwise, the program advances to a step 105. The step 105 decides whether the calculated position of the centroid G is in the OK zone or the NG zone. When the position of the centroid G is decided to be in the OK zone, the program advances from the step 105 to a step 106 which sets a variable representative of the judgment result into an OK-indicating state. After the step 106, the program advances to a step 108. When the position of the centroid G is decided to be in the NG zone, the program advances from the step 105 to a step 107 which sets the judgment-result variable into an NG-indicating state. After the step 107, the program advances to the step 108. The step 108 decides whether or not a solder portion to be inspected next is present by referring to data of solder portions which is previously inputted into the computer 8 by the user. When such a next solder portion is present, the program returns to the step 101 so that the next solder portion will be similarly subjected to the previously-mentioned inspecting processes.

When such a next solder portion is absent, the program advances to a step 109 which outputs the judgment results to a suitable device (not shown), for example, a display or a printer.

The step 201 activates the close inspection device including the laser illumination device 17 and the light receiver 18 to execute the close inspection. The light receiver 18 outputs the height data which is stored into the frame memory 8D. The step 201 decides whether the solder portion is good or poor (OK or NG) by processing the height data as described previously. A step 202 following the step 201 changes and tunes the membership functions in accordance with the result of the close-inspection judgment which is obtained at the step 201. As will be explained later, the membership functions are used in the fuzzy inference block 103 and another fuzzy inference block 203. The block 203 which follows the step 202 processes the data of the image "B" in accordance with fuzzy inference, and thereby calculates a final composite shape (figure) Σa and the position of the centroid G of the final composite shape Σa. In addition, the block 203 decides whether the calculated position of the centroid G is in the OK zone, the NG zone, or the gray zone. The details of the block 103 will be explained later. A step 204 following the block 203 decides whether or not the result of the fuzzy-inference judgement executed at the block 203 agrees with the result of the close-inspection judgment executed at the step 201. When the result of the fuzzy-inference judgement agrees with the result of the close-inspection judgment, the program advances to the step 108. Otherwise, the program returns to the step 202. As a result, the membership functions continue to be tuned until the result of the fuzzy-inference judgement will agree with the result of the close-inspection judgment.

Figure 16:
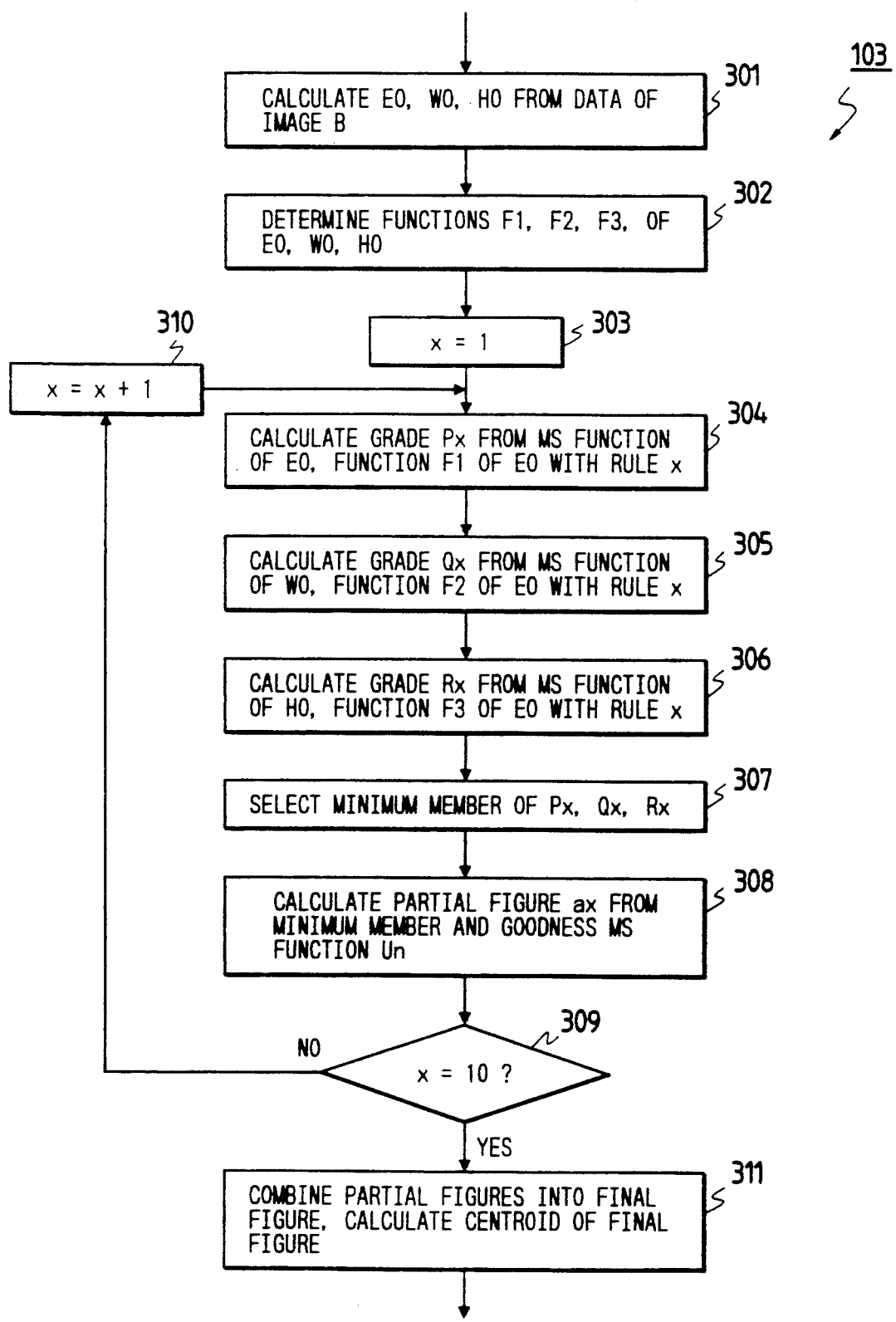
FIGS. 16 and 17 are flowcharts showing steps in the blocks of FIG. 15.

As shown in FIG. 16, a first step 301 of the fuzzy-inference block 103 which follows the step 102 of FIG. 15 calculates the values of the goodness/poorness judgment factors EO, WO, and HO from the data of the image "B". A step 302 determines the triangular-shape functions F1, F2, and F3 (see FIG. 8) on the basis of the calculated values of the goodness/poorness judgment factors EO, WO, and HO respectively. A step 303 following the step 302 sets a variable "x" to 1. The variable "x" represents a natural number of 1 to 10 which identifies the rules 1-10. The step 303 is followed by a step 304 which calculates the grade Px at the point of intersection between the triangular-shape function F1 of the goodness/poorness judgment factor EO and the membership function of the goodness/poorness judgment factor EO with respect to the rule "x". A step 305 following the step 304 calculates the grade Qx at the point of intersection between the triangular-shape function F2 of the goodness/poorness judgment factor WO and the membership function of the goodness/poorness judgment factor WO with respect to the rule "x". A step 306 following the step 305 calculates the grade Rx at the point of intersection between the triangular-shape function F3 of the goodness/poorness judgment factor HO and the membership function of the goodness/poorness judgment factor HO with respect to the rule "x". A step 307 following the step 306 selects the minimum member of the calculated grades Px, Qx, and Rx. A step 308 following the step 307 calculates the partial region ax from the selected minimum member of the grades Px, Qx, and Rx, and the goodness-degree membership function Un (Un=U1, U2, ..., U7) with respect to the rule "x" as described previously. A step 309 following the step 308 compares the number "x" with 10. When the number "x" differs from 10, the program advances to a step 310. When the number "x" is equal to 10, the program advances to a step 311. The step 310 executes the statement "x=x+1", and thus increments the number "x" by 1. After the step 310, the program returns to the step 304. Thus, the sequence of the steps 304-309 is periodically reiterated until the number "x" reaches 10. As a result, the partial regions a1, a2, ..., a10 are calculated. The step 311 adds and combines the partial regions a1, 2, a3, a4, a5, a6, a7, a8, a9, and a10 into a final composite shape (figure) Σa. In addition, the step 311 calculates the position of the centroid G of the final accumulative shape Σa. The step 311 is followed by the step 104 of FIG. 15.

Figure 17:
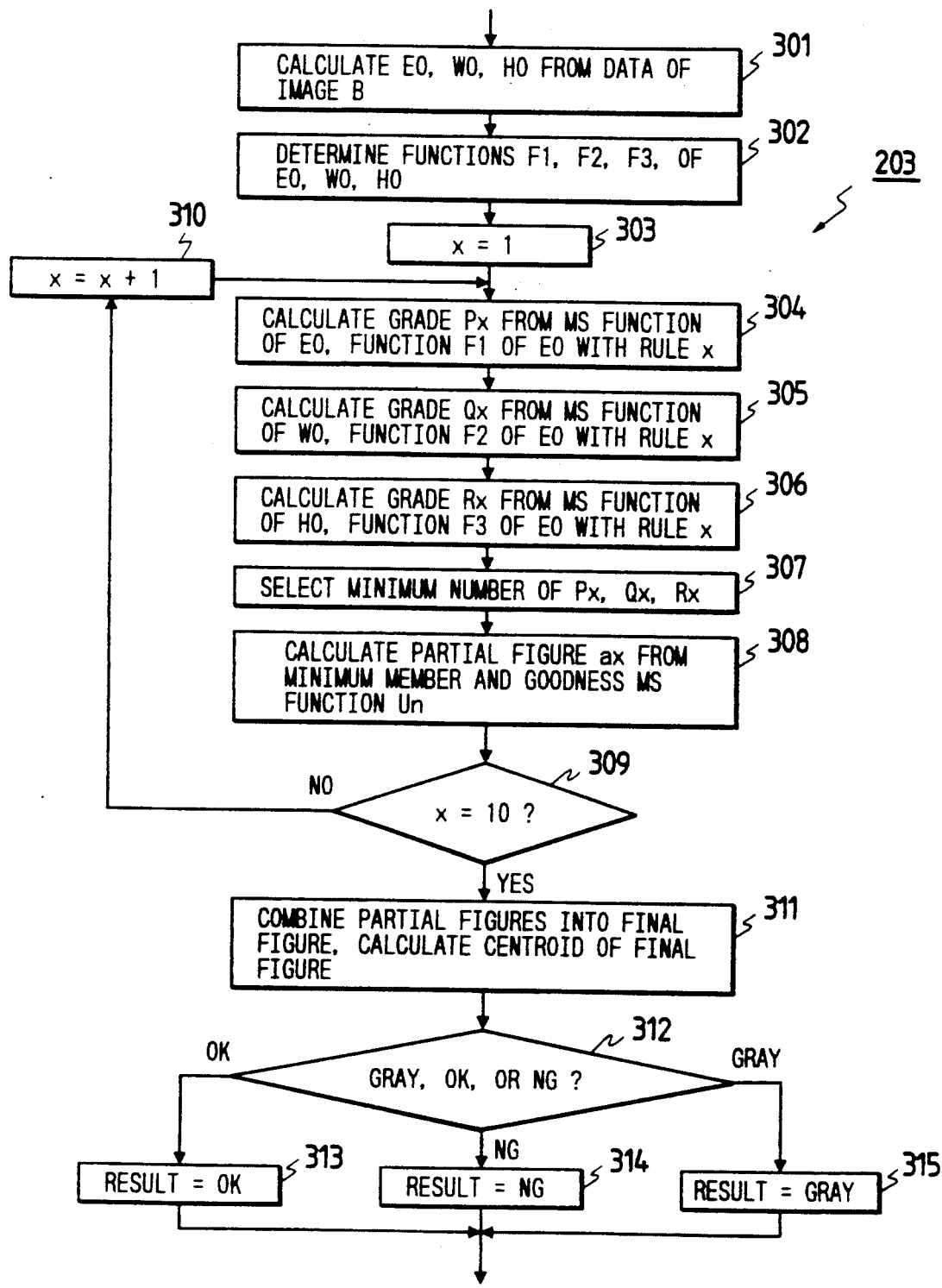

FIG. 17 shows the details of the fuzzy-inference block 203 which is similar to the fuzzy-inference block 103 of FIG. 16 except that steps 312-315 are added. A first step 301 of the fuzzy-inference block 203 of FIG. 17 follows the step 202 of FIG. 15. As shown in FIG. 17, the step 312 which follows the step 311 decides whether the calculated position of the centroid G is in the OK zone, the NG zone, or the gray zone. When the position of the centroid G is decided to be in the OK zone, the program advances to a step 313. When the position of the centroid G is decided to be in the NG zone, the program advances to a step 314. When the position of the centroid G is decided to be in the gray zone, the program advances to a step 315. The step 313 sets the judgment-result variable into the OK-indicating state. The step 314 sets the judgment-result variable into the NG-indicating state. The step 315 sets the judgment-result variable into the gray-indicating state. The steps 313, 314, and 315 are followed by the step 204 of FIG. 15.

It should be noted that this embodiment may be modified in various ways. For example, a modification of this embodiment uses rough rules 11-14 in addition to the previously-mentioned rules 1-10, and executes the fuzzy inference by referring to the rough rules 11-14 also. The details of the rough rules 11-14 will be given in the following.

Rule 11: If EO is small (S), then an inspected solder portion may be good at a somewhat high possibility.

Rule 12: If EO is middle (M), then an inspected solder portion may be good at an intermediate possibility.

Rule 13: If EO is large (L), then an inspected solder portion may be good at a somewhat low possibility.

Rule 14: If HO is small (S), then an inspected solder portion may be good at a high possibility.

What is claimed is:

1. An apparatus for automatically inspecting a solder portion of a device comprising:

a source of light for illuminating the solder portion of said device;

a camera for providing a signal representing an image of the solder portion;

a computer means for receiving said signal from said camera, said computer means including a program memory, a central processing unit, a first frame memory receiving said signal from said camera and a second frame memory;

control means, responsive to an output from said computer means, for controlling movement of said camera;

a source of laser light;

means for directing said laser light to said solder portion of said device; and detection means for receiving reflected laser light from said solder portion of said device and outputting a signal representing a condition of said solder portion to said second frame memory; wherein said computer means includes means for calculating values of goodness/poorness judgment factors from the signal representing an image of the solder portion, means for calculating grades of the goodness/poorness judgment factors from the calculated values of the goodness/poorness judgment factors and from predetermined membership functions of the goodness/poorness judgment factors according to predetermined rules each having a condition part related to the goodness/poorness judgment factors and a conclusion part related to a goodness degree, means for calculating partial figures from predetermined membership functions of the goodness degree and from the calculated grades of the goodness/poorness judgment factors, means for combining the partial figures into a final figure, means for calculating a position of a centroid of the final figure, and means for deciding whether or not the solder portion is good on the basis of the calculated position of the centroid with respect to a predetermined judgment scale.

2. The apparatus of claim 1, wherein the means for calculating values of goodness/poorness judgment factors comprises means for dividing the image of the solder portion into a bright region and a dark region, means for calculating an area and width of the bright region, and means for calculating the values of goodness/poorness judgment factors from the area and the width of the bright region.

3. The apparatus of claim 1, wherein the judgment scale has a gray zone, and the means for deciding includes means for deciding whether or not the solder portion is in the gray zone, and when the solder portion is decided to be in the gray zone, deciding whether or not the solder portion is good using the signal representing a condition of said solder portion from the detection means.

4. The apparatus of claim 3, further comprising means for correcting the membership function in accordance with the signal representing a condition of said solder portion from the detection means.

5. An apparatus for automatically inspecting a solder portion of a device comprising:

a source of light for illuminating the solder portion of said device;

a camera for providing a signal representing a first condition of the solder portion;

a computer means for receiving said signal from said camera, said computer means including a program memory, a central processing unit, a first frame memory receiving said signal from said camera and a second frame memory;

a source of laser light;

means for directing said laser light to said solder portion of said device; and detection means for receiving reflected laser light from said solder portion of said device and outputting a signal representing a second condition of the solder portion to said second frame memory; wherein said computer means includes means for calculating a first grade from the signal representing the first condition of the solder portion in accordance with a first predetermined membership function which determines a relation between the first grade and the condition of the solder portion, means for calculating a first parameter representative of a goodness degree from the first grade calculated by the means for calculating a first grade and from a second predetermined membership function corresponding to a first rule which has a condition part related to the condition of the solder portion and a conclusion part related to the goodness degree, means for calculating a second grade from the signal representing a condition of the solder portion in accordance with a third predetermined membership function which determines a relation between the second grade and the condition of the solder portion, means for calculating a second parameter representative of the goodness degree from the second grade calculated by the second-grade calculating means and from a fourth predetermined membership function corresponding to a second rule which has a condition part related to the condition of the solder portion and a conclusion part related to the goodness degree, and means for deciding whether the solder portion is good or poor in response to the first parameter calculated by the first parameter calculating means and the second parameter calculated by the second-parameter calculating means.

6. An apparatus for automatically inspecting a solder portion of a device comprising:

a source of light for illuminating the solder portion of said device;

a camera for providing a signal representing a first condition of the solder portion;

a computer means for receiving said signal from said camera, said computer means including a program memory, a central processing unit, a first frame memory receiving said signal from said camera and a second frame memory;

a source of laser light;

means for directing said laser light to said solder portion of said device; and detection means for receiving reflected laser light from said solder portion of said device and outputting a signal representing a second condition to said second frame memory; wherein said computer means includes means for deciding whether the solder portion is good, poor, or gray in response to the signal representing the first condition of the solder portion, means for, when the solder portion is decided to be gray, deciding whether the solder portion is good or poor in response to the signal representing the second condition of the solder portion.

7. A method of inspecting a solder portion of a device with an apparatus including a source of light, a camera solder portion, a computation circuit having a program memory, a central processing unit, a first frame memory receiving said signal from said camera and a second frame memory, a source of laser light, means for directing said laser light to said solder portion of said device, and means for detecting reflected laser light from said solder portion and outputting a signal corresponding to a condition of said solder portion to said second frame memory, said method comprising the steps of:

illuminating the solder portion of said device with the source of light providing a signal from said camera representing an image of the solder portion;

storing said signal in said first frame memory of the computer means;

calculating values of goodness/poorness judgment factors from the stored image signal;

calculating grades of the goodness/poorness judgment factors from the calculated values of the goodness/poorness judgment factors and from predetermined membership functions of the goodness/poorness judgment factors according to predetermined rules each having a condition part related to the goodness/poorness judgment factors and a conclusion part related to a goodness degree;

calculating partial figures from predetermined membership functions of the goodness degree and from the calculated grades of the goodness/poorness judgment factors;

combining the partial figures into a final figure;

calculating a position of a centroid of the final figure; and deciding whether or not the solder portion is good on the basis of the calculated position of the centroid with respect to a predetermined judgment scale.

8. The method of claim 7, wherein the step of calculating values of goodness/poorness judgment factors comprises the steps of dividing the image of the solder portion into a bright region and a dark region, calculating an area and a width of the bright region, and calculating the values of the goodness/poorness judgment factors from the area and width of the bright region.

9. The method of claim 7, wherein the judgment scale has a gray zone, and the step of deciding comprises the steps of deciding whether or not the solder portion is in the gray zone, and further comprising the step of, when the solder portion is decided to be in the gray zone, deciding whether or not the solder portion is good using the signal representing a condition of said solder portion from the detecting means.

10. The method of claim 9, further comprising the step of correcting the membership function in accordance with the signal representing a condition of said solder portion from the detecting means.

* * * * *